(12) United States Patent
Casalnuovo et al.

(10) Patent No.: US 11,339,138 B2
(45) Date of Patent: May 24, 2022

(54) PROCESS AND INTERMEDIATES FOR THE PREPARATION OF CERTAIN NEMATICIDAL SULFONAMIDES

(71) Applicant: E. I. DU PONT DE NEMOURS AND COMPANY, Wilmington, DE (US)

(72) Inventors: Albert Loren Casalnuovo, Wilmington, DE (US); Ty Wagerle, West Chester, PA (US); Jun Yan, Newark, DE (US); Erin Demko, Wilmington, DE (US); Matthew Richard Oberholzer, Wilmington, DE (US); Rafael Shapiro, Wilmington, DE (US)

(73) Assignee: E. I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 17/281,370

(22) PCT Filed: Oct. 2, 2019

(86) PCT No.: PCT/US2019/054255
§ 371 (c)(1),
(2) Date: Mar. 30, 2021

(87) PCT Pub. No.: WO2020/072616
PCT Pub. Date: Apr. 9, 2020

(65) Prior Publication Data
US 2021/0309621 A1    Oct. 7, 2021

Related U.S. Application Data

(60) Provisional application No. 62/741,877, filed on Oct. 5, 2018.

(51) Int. Cl.
*C07D 291/08*       (2006.01)
*C07C 303/06*       (2006.01)
*C07D 471/04*       (2006.01)

(52) U.S. Cl.
CPC .......... *C07D 291/08* (2013.01); *C07C 303/06* (2013.01); *C07D 471/04* (2013.01)

(58) Field of Classification Search
CPC .... C07D 291/08; C07D 471/04; C07C 303/06
See application file for complete search history.

(56) References Cited

FOREIGN PATENT DOCUMENTS

| CN | 105481735 B | 1/2018 |
| CN | 1084404447 A | 8/2018 |

(Continued)

OTHER PUBLICATIONS

Burmistrov & Chekhuta, 1(10) Zhurnal Organicheskoi Khimii 1852-4 (1965) (Year: 1965).*

(Continued)

*Primary Examiner* — Timothy R Rozof

(57) ABSTRACT

The present invention provides a method for preparing a compound of Formula C, Formula D, or Formula F:

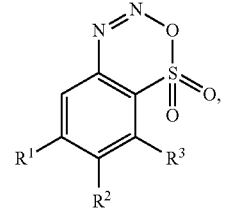

Formula C

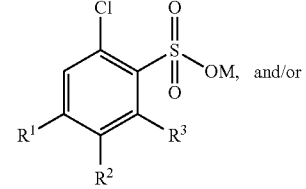

Formula D

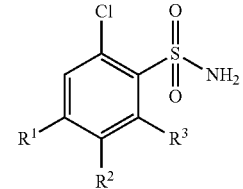

Formula F wherein each $R^1$, $R^2$, and $R^3$ is independently H, $SF_5$, $N(C_1-C_8$ alkyl)$(C_1-C_8$ alkyl), $C(=S)N(C_1-C_8$ alkyl)$(C_1-C_8$ alkyl), $SO_2N(C_1-C_8$ alkyl)$(C_1-C_8$ alkyl), $OSO_2(C_1-C_8$ alkyl), $OSO_2N(C_1-C_8$ alkyl)$(C_1-C_8$ alkyl), $N(C_1-C_8$ alkyl)$SO_2(C_1-C_8$ alkyl), or $C_1-C_8$ alkyl, $C_1-C_8$ haloalkyl, $C_2-C_8$ alkenyl, $C_2-C_8$ alkynyl, $C_3-C_{10}$ cycloalkyl, $C_3-C_{10}$ halocycloalkyl, $C_4-C_{10}$ alkylcycloalkyl, $C_4-C_{10}$ cycloalkylalkyl, $C_6-C_{14}$ cycloalkylcycloalkyl, $C_5-C_{10}$ alkylcycloalkylalkyl, $C_3-C_8$ cycloalkenyl, $C_1-C_8$ alkoxy, $C_1-C_8$ haloalkoxy, $C_3-C_8$ cycloalkoxy, $C_3-C_8$ halocycloalkoxy, $C_4-C_{10}$ cycloalkylalkoxy, $C_2-C_8$ alkenyloxy, $C_2-C_8$ alkynyloxy, $C_1-C_8$ alkylthio, $C_1-C_8$ alkylsulfinyl, $C_1-C_8$ alkylsulfonyl, $C_3-C_8$ cycloalkylthio, $C_3-C_8$ cycloalkylsulfinyl, $C_3-C_8$ cycloalkylsulfonyl, $C_4-C_{10}$ cycloalkylalkylthio, $C_4-C_{10}$ cycloalkylalkylsulfinyl, $C_4-C_{10}$ cycloalkylalkylsulfonyl, $C_2-C_8$ alkenylthio, $C_2-C_8$ alkenylsulfinyl, $C_2-C_8$ alkenylsulfonyl, $C_2-C_8$ alkynylthio, $C_2-C_8$ alkynylsulfinyl, $C_2-C_8$ alkynylsulfonyl, or phenyl; or two of $R^1$, $R^2$, and $R^3$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and such ring is optionally substituted with up to 3 substituents independently selected from the group consisting of $C_1-C_4$ alkyl, $C_1-C_4$ haloalkyl, $C_2-C_4$ alk- (Continued)

enyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl; and M is an inorganic cation or organic cation.

5 Claims, No Drawings

(56) References Cited

FOREIGN PATENT DOCUMENTS

| | | |
|---|---|---|
| WO | 2010/070008 A1 | 6/2010 |
| WO | 2013/055584 A1 | 4/2013 |

OTHER PUBLICATIONS

Tanaka et al.; 'A new entry for the oxidation of fluoroalkyl-substituted methanol derivatives; Scope and limitation of the organoiodine(V) reagent-catalyzed oxidation'; Journal of Fluorine Chemistry, Mar. 16, 2012 (Mar. 16, 2012); vol. 137, pp. 99-104; p. 102.

* cited by examiner

PROCESS AND INTERMEDIATES FOR THE PREPARATION OF CERTAIN NEMATICIDAL SULFONAMIDES

CROSS-REFERENCE TO RELATED APPLICATIONS

This application claims the benefit of, and priority from, U.S. provisional application Ser. No. 62/741,877, which was filed on Oct. 5, 2018. The contents of the above-identified application are hereby incorporated by reference in its entirety.

BACKGROUND

Certain nematicidal sulfonamides and methods for preparing them have been previously disclosed in, for example, WO 2010/129500, WO 2012/054233, and WO 2014/109933. However, certain synthesis steps disclosed previously still have certain disadvantages. Thus there remains a need for alternative ways of preparing certain nematicidal sulfonamides.

SUMMARY

In one aspect, the present invention provides a method for preparing a compound of Formula C, Formula D, or Formula F:

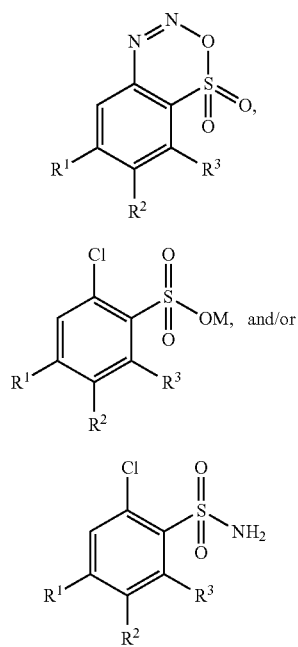

wherein each $R^1$, $R^2$, and $R^3$ is independently H, $SF_5$, $N(C_1\text{-}C_8 \text{ alkyl})(C_1\text{-}C_8 \text{ alkyl})$, $C(=S)N(C_1\text{-}C_8 \text{ alkyl})(C_1\text{-}C_8 \text{ alkyl})$, $SO_2N(C_1\text{-}C_8 \text{ alkyl})(C_1\text{-}C_8 \text{ alkyl})$, $OSO_2(C_1\text{-}C_8 \text{ alkyl})$, $OSO_2N(C_1\text{-}C_8 \text{ alkyl})(C_1\text{-}C_8 \text{ alkyl})$, $N(C_1\text{-}C_8 \text{ alkyl})SO_2(C_1\text{-}C_8 \text{ alkyl})$, or $C_1\text{-}C_8$ alkyl, $C_1\text{-}C_8$ haloalkyl, $C_2\text{-}C_8$ alkenyl, $C_2\text{-}C_8$ alkynyl, $C_3\text{-}C_{10}$ cycloalkyl. $C_3\text{-}C_{10}$ halocycloalkyl, $C_4\text{-}C_{10}$ alkylcycloalkyl, $C_4\text{-}C_{10}$ cycloalkylalkyl, $C_6\text{-}C_{14}$ cycloalkylcycloalkyl, $C_5\text{-}C_{10}$ alkylcycloalkylalkyl, $C_3\text{-}C_8$ cycloalkenyl, $C_1\text{-}C_8$ alkoxy. $C_1\text{-}C_8$ haloalkoxy, $C_3\text{-}C_8$ cycloalkoxy, $C_3\text{-}C_8$ halocycloalkoxy, $C_4\text{-}C_{10}$ cycloalkylalkoxy, $C_2\text{-}C_8$ alkenyloxy, $C_2\text{-}C_8$ alkynyloxy, $C_1\text{-}C_8$ alkylthio, $C_1\text{-}C_8$ alkylsulfinyl, $C_1\text{-}C_8$ alkylsulfonyl, $C_3\text{-}C_8$ cycloalkylthio, $C_3\text{-}C_8$ cycloalkylsulfinyl, $C_3\text{-}C_8$ cycloalkylsulfonyl, $C_4\text{-}C_{10}$ cycloalkylalkylthio, $C_4\text{-}C_{10}$ cycloalkylalkylsulfinyl, $C_4\text{-}C_{10}$ cycloalkylalkylsulfonyl, $C_2\text{-}C_8$ alkenylthio, $C_2\text{-}C_8$ alkenylsulfinyl, $C_2\text{-}C_8$ alkenylsulfonyl, $C_2\text{-}C_8$ alkynylthio, $C_2\text{-}C_8$ alkynylsulfinyl, $C_2\text{-}C_8$ alkynylsulfonyl, or phenyl; or two of $R^1$, $R^2$, and $R^3$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and such ring is optionally substituted with up to 3 substituents independently selected from the group consisting of $C_1\text{-}C_4$ alkyl, $C_1\text{-}C_4$ haloalkyl, $C_2\text{-}C_4$ alkenyl, $C_2\text{-}C_4$ haloalkenyl, $C_2\text{-}C_4$ alkynyl, $C_2\text{-}C_4$ haloalkynyl, $C_3\text{-}C_7$ cycloalkyl, $C_3\text{-}C_7$ halocycloalkyl, $C_4\text{-}C_8$ alkylcycloalkyl, $C_4\text{-}C_8$ haloalkylcycloalkyl, $C_4\text{-}C_8$ cycloalkylalkyl, $C_4\text{-}C_8$ halocycloalkylalkyl, $C_1\text{-}C_8$ alkoxy, $C_1\text{-}C_8$ haloalkoxy, $C_2\text{-}C_8$ alkoxycarbonyl, $C_2\text{-}C_6$ haloalkoxycarbonyl, $C_2\text{-}C_6$ alkylcarbonyl and $C_2\text{-}C_6$ haloalkylcarbonyl; and M is an inorganic cation or organic cation; comprising:

(a) contacting a compound of Formula A

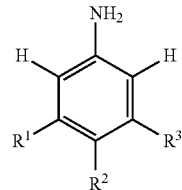

with a solvent selected from o-dichlorobenzene (ODCB), chloroalkanes, and chloroarenes, and a first acid selected from sulfonic acids (for example chlorosulfonic acid $ClSO_3H$), sulfuric acid ($H_2SO_4$), and oleum to form a compound of Formula B:

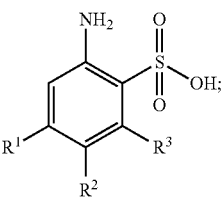

and (b) contacting the compound of Formula B with (i) a nitrite salt $MNO_2$ [for example $NaNO_2$] or nitrite ester (for example alkyl nitrite including tert-butyl nitrite ($tBuNO_2$)] and (ii) a second acid selected from at least one inorganic acid (for example hydrochlorodic acid HCl), at least one organic acid, or mixtures thereof to form a compound of Formula C:

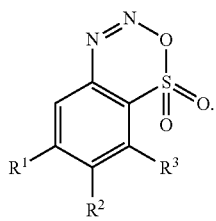

Formula C

Compounds of Formula C can be shown in alterative chemical structures as equilibrium below:

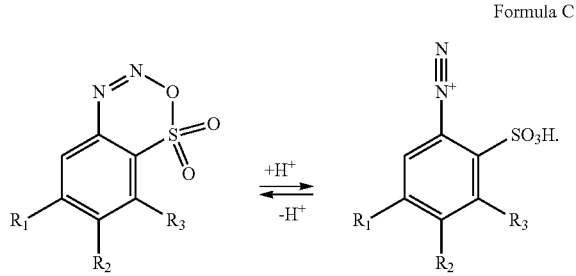

Formula C

In some embodiments, $R^1$, $R^2$, and $R^3$ are not halogen.

In some embodiments, each $R^1$, $R^2$, and $R^3$ is independently H, $C_1$-$C_6$ alkyl, $C_1$-$C_6$ haloalkyl, $C_1$-$C_6$ alkoxy, $C_1$-$C_6$ haloalkoxy, or phenyl. In some embodiments, $R^1$ and $R^3$ are H. In some embodiments, $R^2$ is $C_1$-$C_6$ alkyl, $C_1$-$C_6$ haloalkyl, $C_1$-$C_6$ alkoxy, or $C_1$-$C_6$ haloalkoxy. In some embodiments, $R^2$ is $CH_3$, $CH_2CH_3$, $CF_3$, $OCH_3$, $OCF_3$, or $OCH_2CH_3$. In some embodiments, $R^2$ is $OCH_3$.

In some embodiments, M is an inorganic cation selected from sodium, potassium, ammonium, lithium, and mixtures thereof. In some embodiments. M is sodium. In some embodiments, M is an organic cation selected from trimethylammonium, triethylammonium, tri-n-propylanmnonium, triisopropylammonium, and tributylammonium.

In some further embodiments, the second acid comprises an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some further embodiments, the second acid comprises an organic acid selected from formic acid, acetic acid, propionic acid, citric acid, malic acid, and sulfonic acids. Examples of sulfonic acids including para-toluenesulfonic acid, methanesulfonic acid, and toluenesulfonic acid as a mixture of isomers. In some embodiments, the second acid comprises hydrochloric acid (HCl).

In some embodiments, the methods provided further comprise Step (c) to prepare a compound of Formula D:
(c) contacting the compound of Formula C from Step (b) with a source of copper selected from copper (Cu) powder and copper salts (for example CuI, CuBr, CuCl, or $CuCl_2$), and optionally a first source of chloride if not already provided followed by a first base selected from at least one inorganic base (for example NaOH), at least one organic base, or mixtures thereof to form a compound of Formula D:

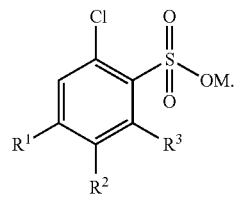

Formula D

In some embodiments, the inorganic base is selected from ammonia, sodium hydroxide, and potassium hydroxide. In some embodiments, the inorganic base is sodium hydroxide. In some embodiments, the organic base is selected from sodium methoxide, sodium ethoxide, sodium iso-propoxide, sodium n-propoxide, potassium methoxide, potassium ethoxide, potassium 1-propoxide, potassium 2-propoxide, methylamine, ethylamine, dimethyl amine, trimethylamine, triethylamine, and pyridine. In some embodiments, the first base comprises sodium methoxide or ammonia (ammonium hydroxide or $NH_4OH$).

The optional first source of chloride can be selected from thionyl chloride ($SOCl_2$), $POCl_3$, $PCl_5$, oxalyl chloride, and phosgene, or any salts or acids containing the chloride, for example NaCl (or MCI where M is an organic cation or inorganic cation as defined herein) or HCl.

In some embodiments, the methods provided further comprise Step (d) to prepare a compound of Formula E:
(d) contacting the compound of Formula D from Step (c) with a second source of chloride selected from thionyl chloride ($SOCl_2$), $POCl_3$, $PCl_5$, oxalyl chloride, and phosgene, and a catalyst selected from N,N-disubstituted formamides (for example dimethylformamide (DMF) and/or N-formylpiperidine) in a solvent S1 to form the compound of Formula E:

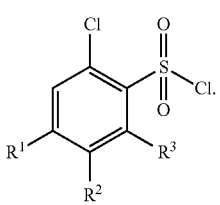

Formula E

In some embodiments, the solvent S1 is selected from water, $C_7$-$C_{10}$ aromatic hydrocarbons, haloalkanes, halogenated benzenes, $C_5$-$C_{10}$ aliphatic hydrocarbons, $C_5$-$C_{10}$ cycloaliphatic hydrocarbons, acetonitrile, or combinations thereof. In some embodiments, the solvent S1 is water, toluene, dichloromethane, 1,2-dichloroethane, 1-chlorobutane, acetonitrile, or combinations thereof. In some embodiments, the solvent S1 is toluene. In some embodiments, the solvent S1 is acetonitrile. In some embodiments, the solvent S1 is a mixture of water and acetonitrile. In some embodiments, the solvent S1 is a mixture of acetonitrile and toluene.

In some embodiments, the methods provided further comprise Step (e) to prepare a compound of Formula F:
(e) contacting the compound of Formula E from Step (d) with a second base selected from ammonia (ammonium hydroxide or $NH_4OH$), trimethylamine, triethylamine, and mixtures thereof, and an optional inorganic base or organic base in a solvent S2 to form the compound of Formula F:

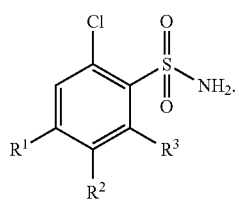

Formula F

In some embodiments, the inorganic base is selected from sodium hydroxide and potassium hydroxide. In some embodiments, the inorganic base is sodium hydroxide. In some embodiments, the organic base is selected from sodium methoxide, sodium ethoxide, sodium iso-propoxide, sodium n-propoxide, potassium methoxide, potassium ethoxide, potassium 1-propoxide, potassium 2-propoxide, and pyridine. In some embodiments, the organic base is sodium methoxide.

In some embodiments, the solvent S2 is selected from water, $C_7$-$C_{10}$ aromatic hydrocarbons, haloalkanes, halogenated benzenes, $C_5$-$C_{10}$ aliphatic hydrocarbons, $C_5$-$C_{10}$ cycloaliphatic hydrocarbons, acetonitrile, or combinations thereof. In some embodiments, the solvent S2 is water, toluene, dichloromethane, 1,2-dichloroethane, 1-chlorobutane, acetonitrile, or combinations thereof. In some embodiments, the solvent S2 is acetonitrile. In some embodiments, the solvent S2 is a mixture of water and acetonitrile. In some embodiments, the solvent S2 is a mixture of acetonitrile and toluene.

In some embodiments, the solvent S1 is the same as the solvent S2. In some embodiments, the solvent S1 is different from the solvent S2.

In some embodiments, the invention provides a method for preparing a compound of Formula 1:

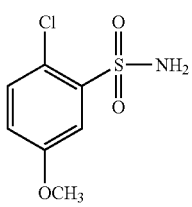

Formula 1 comprising:
(A) contacting a compound of Formula 2

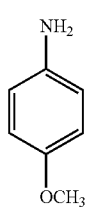

Formula 2 with a solvent selected from o-dichlorobenzene (ODCB), chloroalkanes, and chloroarenes, and a first acid selected from sulfonic acids (for example chlorosulfonic acid $ClSO_3H$), sulfuric acid ($H_2SO_4$), and oleum to form a compound of Formula 3:

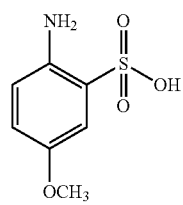

Formula 3

(B) contacting the compound of Formula 3 with (i) a nitrite salt $MNO_2$ [for example $NaNO_2$] or nitrite ester (for example alkyl nitrite including tert-butyl nitrite ($tBuNO_2$)] and (ii) a second acid selected from at least one inorganic acid (for example hydrochlorodic acid HCl), at least one organic acid, or mixtures thereof to form a compound of Formula 4:

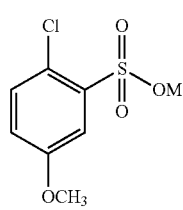

Formula 4 wherein M is an inorganic cation or organic cation;
(C) contacting the compound of Formula 4 with with a source of copper selected from copper (Cu) powder and copper salts (for example CuI, CuBr, CuCl, or $CuCl_2$), and optionally a first source of chloride if not already provided followed by a first base selected from at least one inorganic base (for example NaOH), at least one organic base, or mixtures thereof to form a compound of Formula 5:

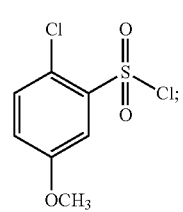

Formula 5

(D) contacting the compound of Formula 5 of step (C) with a second source of chloride selected from thionyl chloride ($SOCl_2$), $POCl_3$, $PCl_5$, oxalyl chloride, and phosgene, and a catalyst selected from N,N-disubstituted formamides (for example dimethylformamide (DMF) and/or N-formylpiperidine) in a solvent S1 to form the compound of Formula 6:

Formula 6

(E) contacting the compound of Formula 6 with a second base selected from ammonia (ammonium hydroxide or NH$_4$OH), trimethylamine, triethylamine, and mixtures thereof, and an optional inorganic base or organic base in a solvent S2 to form the compound of Formula 1.

Compounds of Formula 4 can be shown in alterative chemical structures as equilibrium below:

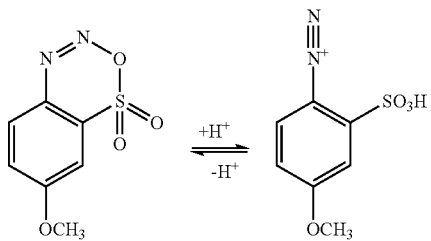

Formula 4

In some embodiments, M is an inorganic cation selected from sodium, potassium, ammonium, lithium, and mixtures thereof. In some embodiments, M is sodium. In some embodiments, M is an organic cation selected from trimethylammonium, triethylammonium, tri-n-propylammonium, triisopropylammonium, and tributylammonium.

In some further embodiments, the second acid comprises an inorganic acid selected from hydrochloric acid (HCl), hydrobromic acid (HBr), phosphoric acid (H$_3$PO$_4$), sulfuric acid (H$_2$SO$_4$), and boric acid (H$_3$BO$_3$). In some further embodiments, the second acid comprises an organic acid selected from formic acid, acetic acid, propionic acid, citric acid, malic acid, and sulfonic acids. Examples of sulfonic acids including para-toluenesulfonic acid, methanesulfonic acid, and toluenesulfonic acid as a mixture of isomers. In some embodiments, the second acid comprises hydrochloric acid (HCl).

In some embodiments, the inorganic base is selected from sodium hydroxide and potassium hydroxide. In some embodiments, the inorganic base is sodium hydroxide. In some embodiments, the organic base is selected from sodium methoxide, sodium ethoxide, sodium iso-propoxide, sodium n-propoxide, potassium methoxide, potassium ethoxide, potassium 1-propoxide, potassium 2-propoxide, and pyridine. In some embodiments, the organic base is sodium methoxide.

The optional first source of chloride can be selected from thionyl chloride (SOCl$_2$), POCl$_3$, PCl$_5$, oxalyl chloride, and phosgene, or any salts or acids containing the chloride, for example NaCl (or MCl where M is an organic cation or inorganic cation as defined herein) or HCl.

In some embodiments, the solvent S1 is selected from water, C$_7$-C$_{10}$ aromatic hydrocarbons, haloalkanes, halogenated benzenes, C$_5$-C$_{10}$ aliphatic hydrocarbons, C$_5$-C$_{10}$ cycloaliphatic hydrocarbons, acetonitrile, or combinations thereof. In some embodiments, the solvent S1 is water, toluene, dichloromethane, 1,2-dichloroethane, 1-chlorobutane, acetonitrile, or combinations thereof. In some embodiments, the solvent S1 is toluene. In some embodiments, the solvent S1 is acetonitrile. In some embodiments, the solvent S1 is a mixture of water and acetonitrile. In some embodiments, the solvent S1 is a mixture of acetonitrile and toluene.

In some embodiments, the solvent S2 is selected from water, C$_7$-C$_{10}$ aromatic hydrocarbons, haloalkanes, halogenated benzenes, C$_5$-C$_{10}$ aliphatic hydrocarbons, C$_5$-C$_{10}$ cycloaliphatic hydrocarbons, acetonitrile, or combinations thereof. In some embodiments, the solvent S2 is water, toluene, dichloromethane, 1,2-dichloroethane, 1-chlorobutane, acetonitrile, or combinations thereof. In some embodiments, the solvent S2 is acetonitrile. In some embodiments, the solvent S2 is a mixture of water and acetonitrile. In some embodiments, the solvent S2 is a mixture of acetonitrile and toluene.

In some embodiments, the solvent S1 is the same as the solvent S2. In some embodiments, the solvent S1 is different from the solvent S2.

In another aspect, the invention provides a method for preparing a compound of Formula G:

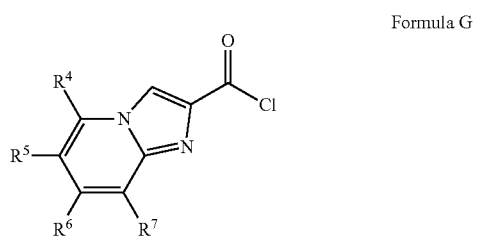

Formula G wherein each $R^4$, $R^5$, $R^6$, and $R^7$ is independently H, halogen, SF$_5$, C(=O)(C$_1$-C$_8$ alkyl), C(=O)O(C$_1$-C$_8$ alkyl), N(C$_1$-C$_8$ alkyl)(C$_1$-C$_8$ alkyl), C(=O)N(C$_1$-C$_8$ alkyl)(C$_1$-C$_8$ alkyl), C(=S)N(C$_1$-C$_8$ alkyl)(C$_1$-C$_8$ alkyl), SO$_2$N(C$_1$-C$_8$ alkyl)(C$_1$-C$_8$ alkyl), OC(=O)(C$_1$-C$_8$ alkyl), OC(=O)O(C$_1$-C$_8$ alkyl), OC(=O)N(C$_1$-C$_8$ alkyl)(C$_1$-C$_8$ alkyl), N(C$_1$-C$_8$ alkyl)C(=O)O(C$_1$-C$_8$ alkyl), N(C$_1$-C$_8$ alkyl)C(=O)N(C$_1$-C$_8$ alkyl)(C$_1$-C$_8$ alkyl), OSO$_2$(C$_1$-C$_8$ alkyl), OSO$_2$N(C$_1$-C$_8$ alkyl)(C$_1$-C$_8$ alkyl), N(C$_1$-C$_8$ alkyl)SO$_2$(C$_1$-C$_8$ alkyl), or C$_1$-C$_8$ alkyl, C$_1$-C$_8$ haloalkyl, C$_2$-C$_8$ alkenyl, C$_2$-C$_8$ alkynyl, C$_3$-C$_{10}$ cycloalkyl, C$_3$-C$_{10}$ halocycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl. C$_1$-C$_8$ alkoxy, C$_1$-C$_8$ haloalkoxy, C$_3$-C$_8$ cycloalkoxy, C$_3$-C$_8$ halocycloalkoxy, C$_4$-C$_{10}$ cycloalkylalkoxy, C$_2$-C$_8$ alkenyloxy, C$_2$-C$_8$ alkynyloxy, C$_1$-C$_8$ alkylthio, C$_1$-C$_8$ alkylsulfinyl, C$_1$-C$_8$ alkylsulfonyl, C$_3$-C$_8$ cycloalkylthio, C$_3$-C$_8$ cycloalkylsulfinyl, C$_3$-C$_8$ cycloalkylsulfonyl, C$_4$-C$_{10}$ cycloalkylalkylthio, C$_4$-C$_{10}$ cycloalkylalkylsulfinyl, C$_4$-C$_{10}$ cycloalkylalkylsulfonyl, C$_2$-C$_8$ alkenylthio, C$_2$-C$_8$ alkenylsulfinyl, C$_2$-C$_8$ alkenylsulfonyl, C$_2$-C$_8$ alkynylthio, C$_2$-C$_8$ alkynylsulfinyl, C$_2$-C$_8$ alkynylsulfonyl, or phenyl; or two of $R^4$, $R^5$, $R^6$, and $R^7$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and such ring is optionally substituted with up to 3 substituents independently selected from the group consisting of C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_8$ alkoxy, C$_1$-C$_8$ haloalkoxy, C$_2$-C$_8$ alkoxycarbonyl, C$_2$-C$_6$ haloalkoxycarbonyl, C$_2$-C$_6$ alkylcarbonyl and C$_2$-C$_6$ haloalkylcarbonyl: comprising contacting a compound of Formula H Formula H

[Structure: imidazo[1,2-a]pyridine with R4, R5, R6, R7 substituents and 2-carboxylic acid (COOH)]

with a source of chloride selected from thionyl chloride (SOCl$_2$), POCl$_3$, PCl$_5$, oxalyl chloride, and phosgene, in the presence of (a) a Reagent A selected from trimethylamine, triethylamine, pyridine, alkylpyridines, and 3-picoline (or 3-methylpyridine), and (b) solvent S3 to form a compound of Formula G:

Formula G

[Structure: imidazo[1,2-a]pyridine with R4, R5, R6, R7 substituents and 2-carbonyl chloride (COCl)]

In some embodiments, the solvent S3 is selected from water, C$_7$-C$_{10}$ aromatic hydrocarbons, haloalkanes, halogenated benzenes, C$_5$-C$_{10}$ aliphatic hydrocarbons, C$_5$-C$_{10}$ cycloaliphatic hydrocarbons, acetonitrile, or combinations thereof. In some embodiments, the solvent S3 is water, toluene, dichloromethane, 1,2-dichloroethane, 1-chlorobutane, acetonitrile, or combinations thereof. In some embodiments, the solvent S3 is toluene. In some embodiments, the solvent S3 is acetonitrile. In some embodiments, the solvent S3 is a mixture of water and acetonitrile. In some embodiments, the solvent S3 is a mixture of acetonitrile and toluene.

In some embodiments, the invention also relates to a method for preparing a compound of Formula 7:

Formula 7

[Structure: 6-CF$_3$-8-Cl-imidazo[1,2-a]pyridine-2-carbonyl chloride]

comprising (a) contacting a compound of Formula 8

Formula 8

[Structure: 6-CF$_3$-8-Cl-imidazo[1,2-a]pyridine-2-carboxylic acid]

with a Reagent A selected from trimethylamine, triethylamine, pyridine, alkylpyridines, and 3-picoline (or 3-methylpyridine) in the presence of solvent S3 to form a compound of Formula 9:

Formula 9

[Structure: 6-CF$_3$-8-Cl-imidazo[1,2-a]pyridine-2-carboxylate anion with [Reagent A-H]+ counterion]

and (b) contacting the compound of Formula 9 with a source of chloride selected from thionyl chloride (SOCl$_2$), POCl$_3$, PCl$_5$, oxalyl chloride, and phosgene to form the compound of Formula 7.

In another aspect, the invention provides a method for preparing a compound of Formula J:

Formula J

[Structure: imidazo[1,2-a]pyridine-2-carboxamide sulfonamide with R1, R2, R3, R4, R5, R6, R7 substituents and Cl on the phenyl ring]

wherein each R$^1$, R$^2$, and R$^3$ is independently H, SF$_5$, N(C$_1$-C$_8$ alkyl)(C$_1$-C$_8$ alkyl), C(=S)N(C$_1$-C$_8$ alkyl)(C$_1$-C$_8$ alkyl), SO$_2$N(C$_1$-C$_8$ alkyl)(C$_1$-C$_8$ alkyl), OSO$_2$(C$_1$-C$_8$ alkyl), OSO$_2$N(C$_1$-C$_8$ alkyl)(C$_1$-C$_8$ alkyl), N(C$_1$-C$_8$ alkyl)SO$_2$(C$_1$-C$_8$ alkyl), or C$_1$-C$_8$ alkyl, C$_1$-C$_8$ haloalkyl, C$_2$-C$_8$ alkenyl, C$_2$-C$_8$ alkynyl, C$_3$-C$_{10}$ cycloalkyl, C$_3$-C$_{10}$ halocycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl, C$_1$-C$_8$ alkoxy, C$_1$-C$_8$ haloalkoxy, C$_3$-C$_8$ cycloalkoxy, C$_3$-C$_8$ halocycloalkoxy, C$_4$-C$_{10}$ cycloalkylalkoxy, C$_2$-C$_8$ alkenyloxy, C$_2$-C$_8$ alkynyloxy, C$_1$-C$_8$ alkylthio, C$_1$-C$_8$ alkylsulfinyl, C$_1$-C$_8$ alkylsulfonyl, C$_3$-C$_8$ cycloalkylthio, C$_3$-C$_8$ cycloalkylsulfinyl, C$_3$-C$_8$ cycloalkylsulfonyl, C$_4$-C$_{10}$ cycloalkylalkylthio, C$_4$-C$_{10}$ cycloalkylalkylsulfinyl, C$_4$-C$_{10}$ cycloalkylalkylsulfonyl, C$_2$-C$_8$ alkenylthio, C$_2$-C$_8$ alkenylsulfinyl, C$_2$-C$_8$ alkenylsulfonyl, C$_2$-C$_8$ alkynylthio, C$_2$-C$_8$ alkynylsulfinyl, C$_2$-C$_8$ alkynylsulfonyl, or phenyl; or two of R$^1$, R$^2$, and R$^3$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and such ring is optionally substituted with up to 3 substituents independently selected from the group consisting of C$_1$-C$_4$ alkyl, C$_1$-C$_4$ haloalkyl, C$_2$-C$_4$ alkenyl. C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_8$ alkoxy, C$_1$-C$_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl, each $R^4$, $R^5$, $R^6$, and $R^7$ is independently H, halogen, $SF_5$, $C(=O)(C_1$-$C_8$ alkyl), $C(=O)O(C_1$-$C_8$ alkyl), $N(C_1$-$C_8$ alkyl)($C_1$-$C_8$ alkyl), $C(=O)N(C_1$-$C_8$ alkyl)($C_1$-$C_8$ alkyl), $C(=S)N(C_1$-$C_8$ alkyl)($C_1$-$C_8$ alkyl), $SO_2N(C_1$-$C_8$ alkyl)($C_1$-$C_8$ alkyl), $OC(=O)(C_1$-$C_8$ alkyl), $OC(=O)O(C_1$-$C_8$ alkyl), $OC(=O)N(C_1$-$C_8$ alkyl)($C_1$-$C_8$ alkyl), $N(C_1$-$C_8$ alkyl)$C(=O)O(C_1$-$C_8$ alkyl), $N(C_1$-$C_8$ alkyl)$C(=O)N(C_1$-$C_8$ alkyl)($C_1$-$C_8$ alkyl), $OSO_2(C_1$-$C_8$ alkyl), $OSO_2N(C_1$-$C_8$ alkyl)($C_1$-$C_8$ alkyl), $N(C_1$-$C_8$ alkyl)$SO_2(C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl, $C_2$-$C_8$ alkynylsulfonyl, or phenyl; or two of $R^4$, $R^5$, $R^6$, and $R^7$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and such ring is optionally substituted with up to 3 substituents independently selected from the group consisting of $C_1$-$C_4$ alkyl, $C_1$-$C_4$ haloalkyl, $C_2$-$C_4$ alkenyl, $C_2$-$C_4$ haloalkenyl. $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl:

comprising (a) contacting a compound of Formula F

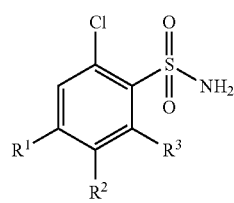

Formula F with a compound of Formula G

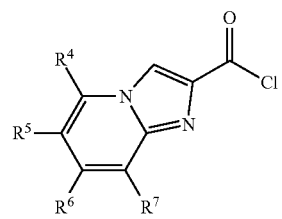

Formula G in the presence of a Reagent B selected from trimethylamine, triethylamine, pyridine, alkylpyridines, and 3-picoline (or 3-methylpyridine) in a solvent S4 to form a compound of Formula K:

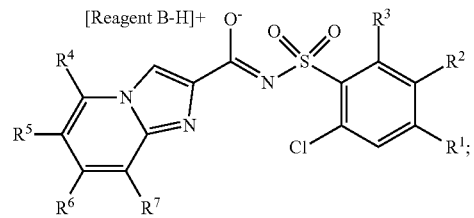

Formula K and (b) contacting the compound of Formula K with an acid A1 in a solvent S5 to form the compound of Formula J.

In some embodiments, the acid A1 is an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some embodiments, the acid A1 comprises hydrochloric acid (HCl). In some other embodiments, the acid A1 comprises an organic acid selected from formic acid, acetic acid, propionic acid, citric acid, malic acid, and sulfonic acids. In some embodiments, the acid A1 comprises sulfonic acids. Examples of sulfonic acids including para-toluenesulfonic acid, methanesulfonic acid, and toluenesulfonic acid as a mixture of isomers. In some embodiments, the contacting step does not use a base.

In some embodiments, the solvent S4 is selected from water ($H_2O$), $C_7$-$C_{10}$ aromatic hydrocarbons, $C_5$-$C_{10}$ aliphatic hydrocarbons, $C_5$-$C_{10}$ cycloaliphatic hydrocarbons, acetonitrile, or combinations thereof. In some embodiments, the solvent S4 is water, toluene, acetonitrile, or combinations thereof. In some embodiments, the solvent S4 is toluene. In some embodiments, the solvent S4 is acetonitrile. In some embodiments, the solvent S4 is a mixture of water and acetonitrile. In some embodiments, the solvent S4 does not include ethers, esters, and/or halogenated hydrocarbons.

In some embodiments, the solvent S5 is selected from water ($H_2O$), $C_7$-$C_{10}$ aromatic hydrocarbons, $C_5$-$C_{10}$ aliphatic hydrocarbons, $C_5$-$C_{10}$ cycloaliphatic hydrocarbons, acetonitrile, or combinations thereof. In some embodiments, the solvent S5 is water, toluene, acetonitrile, or combinations thereof. In some embodiments, the solvent S5 is toluene. In some embodiments, the solvent S5 is acetonitrile. In some embodiments, the solvent S5 is a mixture of water and acetonitrile.

In some embodiments, the solvent S4 and solvent S5 are the same. In some embodiments, the solvent S4 and solvent S5 are different. In some embodiments, the solvent S4 is acetonitrile and the solvent S5 is a mixture of water and acetonitrile. In some embodiments, the solvent S4 is a mixture of water and acetonitrile and the solvent S5 is acetonitrile. In some embodiments, the solvent S4 does not include ethers, esters, and/or halogenated hydrocarbons. In some embodiments, the solvent S5 does not include ethers, esters, and/or halogenated hydrocarbons.

In some embodiments, $R^1$, $R^2$, and $R^3$ are not halogen.

In some embodiments, each $R^1$, $R^2$, and $R^3$ is independently H, $C_1$-$C_6$ alkyl, $C_1$-$C_6$ haloalkyl, $C_1$-$C_6$ alkoxy, $C_1$-$C_6$ haloalkoxy, or phenyl. In some embodiments, $R^1$ and $R^3$ are H. In some embodiments, $R^2$ is $C_1$-$C_6$ alkyl, $C_1$-$C_6$ haloalkyl, $C_1$-$C_6$ alkoxy, or $C_1$-$C_6$ haloalkoxy. In some embodiments, $R^2$ is $CH_3$, $CH_2CH_3$, $CF_3$, $OCH_3$, $OCF_3$, or $OCH_2CH_3$. In some embodiments, $R^2$ is $OCH_3$.

In some embodiments, each $R^4$, $R^5$, $R^6$, and $R^7$ is independently H, $C_1$-$C_6$ alkyl, $C_1$-$C_6$ haloalkyl, $C_1$-$C_6$ alkoxy, $C_1$-$C_6$ haloalkoxy, or phenyl. In some embodiments, $R^1$ and $R^3$ are H. In some embodiments, $R^5$ is $C_1$-$C_6$ alkyl, $C_1$-$C_6$ haloalkyl, $C_1$-$C_6$ alkoxy, or $C_1$-$C_6$ haloalkoxy. In some embodiments, $R^5$ is $CH_3$, $CH_2CH_3$, $CF_3$, $OCH_3$, $OCF_3$, or $OCH_2CH_3$. In some embodiments, $R^5$ is $CF_3$. In some embodiments, $R^7$ is halogen. In some embodiments, $R^7$ is Cl.

In some embodiments, the invention also relates to a method for preparing a compound of Formula 10:

Formula 10

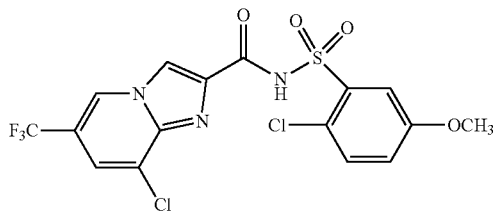

comprising (a) contacting a compound of Formula 1

Formula 1

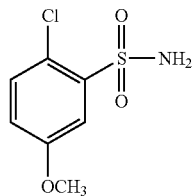

with a compound of Formula 7

Formula 7

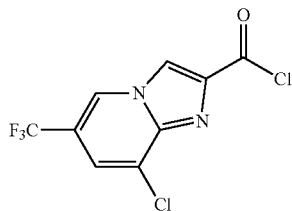

in the presence of a Reagent B selected from trimethylamine, triethylamine, pyridine, alkylpyridines, and 3-picoline (or 3-methylpyridine) in a solvent S4 to form a compound of Formula 11:

Formula 11

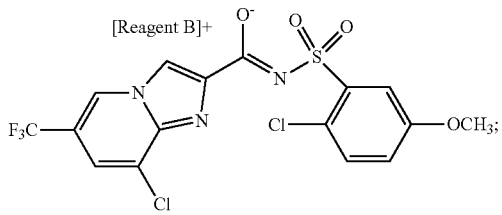

and
(b) contacting the compound of Formula 11 with an acid A1 in a solvent S5 to form the compound of Formula 10.

In some embodiments, the acid A1 is an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some embodiments, the acid A1 comprises hydrochloric acid (HCl). In some other embodiments, the acid A1 comprises an organic acid selected from formic acid, acetic acid, propionic acid, citric acid, malic acid, and sulfonic acids. In some embodiments, the acid A1 comprises sulfonic acids. Examples of sulfonic acids including para-toluenesulfonic acid, methanesulfonic acid, and toluenesulfonic acid as a mixture of isomers. In some embodiments, the method does not use a base.

In some embodiments, the solvent S4 is selected from water ($H_2O$), $C_7$-$C_{10}$ aromatic hydrocarbons, $C_5$-$C_{10}$ aliphatic hydrocarbons, $C_5$-$C_{10}$ cycloaliphatic hydrocarbons, acetonitrile, or combinations thereof. In some embodiments, the solvent S4 is water, toluene, acetonitrile, or combinations thereof. In some embodiments, the solvent S4 is toluene. In some embodiments, the solvent S4 is acetonitrile. In some embodiments, the solvent S4 is a mixture of water and acetonitrile.

In some embodiments, the solvent S5 is selected from water ($H_2O$), $C_7$-$C_{10}$ aromatic hydrocarbons, $C_5$-$C_{10}$ aliphatic hydrocarbons, $C_5$-$C_{10}$ cycloaliphatic hydrocarbons, acetonitrile, or combinations thereof. In some embodiments, the solvent S5 is water, toluene, acetonitrile, or combinations thereof. In some embodiments, the solvent S5 is toluene. In some embodiments, the solvent S5 is acetonitrile. In some embodiments, the solvent S5 is a mixture of water and acetonitrile.

In some embodiments, the solvent S4 and solvent S5 are the same. In some embodiments, the solvent S4 and solvent S5 are different. In some embodiments, the solvent S4 is acetonitrile and the solvent S5 is a mixture of water and acetonitrile. In some embodiments, the solvent S4 is a mixture of water and acetonitrile and the solvent S5 is acetonitrile. In some embodiments, the solvent S4 does not include ethers, esters, and/or halogenated hydrocarbons. In some embodiments, the solvent S5 does not include ethers, esters, and/or halogenated hydrocarbons.

This invention also relates to a compound having a structure of Formula 4 and/or Formula 5:

Formula 4

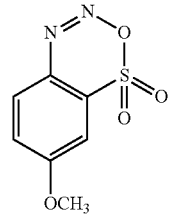

Formula 5

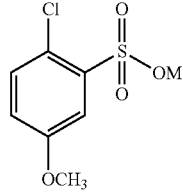

wherein M is an inorganic cation or organic cation.
In some embodiments, M is an inorganic cation selected from sodium, potassium, ammonium, lithium, and mixtures thereof. In some embodiments, M is sodium. In some embodiments, M is an organic cation selected from trimethylammonium, triethylammonium, tri-n-propylammonium, triisopropylammonium, and tributylammonium.

DETAILED DESCRIPTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such phrase would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "ambient temperature" or "room temperature" as used in this disclosure refers to a temperature between about 18° C. and about 28° C.

In the above recitations, the term "alkyl", includes straight-chain or branched alkyl, such as, methyl, ethyl, n-propyl, i-propyl, or the different butyl isomers. As used herein, haloalkanes are alkanes partially or fully substituted with halogen atoms (fluorine, chlorine, bromine or iodine). Examples of haloalkanes include $CH_2Cl_2$, $ClCH_2CH_2Cl$, $ClCH_2CH_2CH_2CH_3$, and $CCl_3CH_3$. Halogenated benzenes are benzenes partially or fully substituted with halogen atoms (fluorine, chlorine, bromine or iodine). Examples of halogenated benzenes include chlorobenzene, 1,2-dichlorobenzene and bromobenzene. $C_7$-$C_{10}$ aromatic hydrocarbons are compounds containing one benzene ring which is substituted with alkyl groups. Examples of $C_7$-$C_{10}$ aromatic hydrocarbons include toluene, xylenes, ethyl benzene and cumene (isopropylbenzene). $C_5$-$C_{10}$ aliphatic hydrocarbons are straight-chain or branched hydrocarbons. Examples of $C_5$-$C_{10}$ aliphatic hydrocarbons include n-hexane, mixed hexanes, n-heptane and mixed heptanes. $C_5$-$C_{10}$ cycloaliphatic hydrocarbons are cyclic hydrocarbons that can be substituted with straight-chain or branched alkyl groups. Examples of $C_5$-$C_{10}$ cycloaliphatic hydrocarbons include cyclopentane, methylcyclopentane, cyclohexane and methylcyclohexane.

The first aspect of the invention provides a method of preparing a compound of Formula 1:

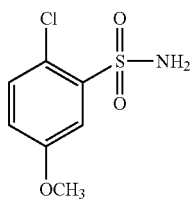

Formula 1

In some embodiments as shown in Scheme 1, a compound of Formula 2 can be converted to the arylsulfonic acid compound of Formula 3 via reaction with sulfuric acid. Next the compound of Formula 3 can be diazotized to form a compound of Formula 4, which can then be converted to the chloroarylsulfonate sodium salt compound of Formula 5 via a Sandmeyer reaction, wherein M is an inorganic cation or organic cation. Next the compound of Formula 5 can be converted to the chloroarylsulfonyl chloride compound of Formula 6 with thionyl chloride and catalytic dimethylformamide (DMF). Subsequent addition of aqueous ammonia can result in a compound of Formula 1.

Scheme 1

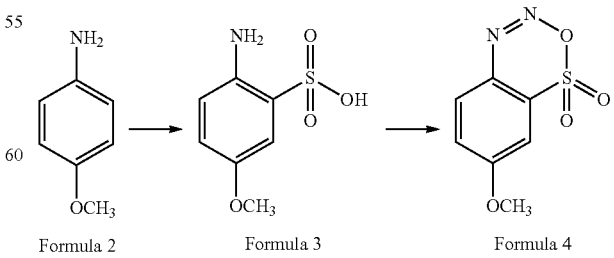

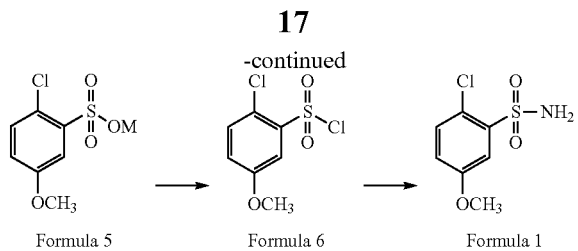

Formula 5 → Formula 6 → Formula 1

In some embodiments, M is an inorganic cation selected from sodium, potassium, ammonium, lithium, and mixtures thereof. In some embodiments, M is sodium. In some embodiments, M is an organic cation selected from trimethylammonium, triethylammonium, tri-n-propylammonium, triisopropylammonium, and tributylammonium.

The reactions shown in Scheme 1 can be accomplished in a solvent is selected from water, $C_7$-$C_{10}$ aromatic hydrocarbons, haloalkanes, halogenated benzenes, $C_5$-$C_{10}$ aliphatic hydrocarbons, $C_5$-$C_{10}$ cycloaliphatic hydrocarbons, acetonitrile, or combinations thereof. In some embodiments, water, toluene, dichloromethane, 1,2-dichloroethane, 1-chlorobutane, acetonitrile, or combinations thereof can be used. Other suitable solvent include xylenes, ethylbenzene, and cumene.

The reactions shown in Scheme 1 can be conducted under a broad range of temperatures, i.e., temperatures in the range from 20° C. to 150° C.; or from 50° C. to 200° C. Temperatures in the range from 50° C. to 180° C.; or from 60° C. to 100° C. are particularly useful. Temperatures in the range of 60° C. to 80° C. are especially useful.

The process shown in Scheme 1 is more efficient and reduces the cost of production for the compound of Formula 1 as compared to previously disclosed processes. Other advantages include safer process by avoiding pyrophoric reagents, better volume efficiency, better reaction kinetics, and/or reduced foaming problem.

The second aspect of the invention provides a method of preparing a compound of Formula 7:

Formula 7

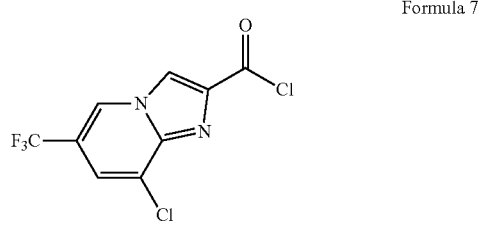 [SMILES: O=C(Cl)c1cn2cc(C(F)(F)F)cc(Cl)c2n1]

In some embodiments as shown in Scheme 2, a compound of Formula 8 can be converted to the acid chloride compound of Formula 7 via an amine salt compound of Formula 9. A Reagent A selected from trimethylamine, triethylamine, pyridine, alkylpyridines, and 3-picoline (or 3-methylpyridine) can be used in this conversion process.

Scheme 2

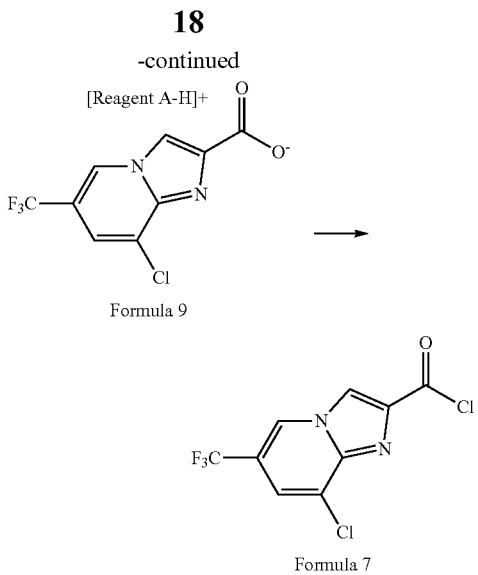

Formula 8

Formula 9

Formula 7

The third aspect of the invention provides a method of preparing a compound of Formula 10:

Formula 10

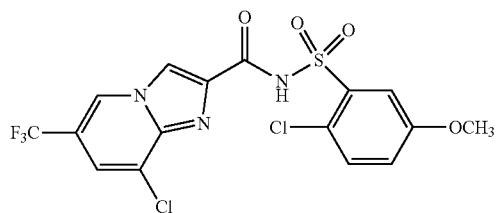

In some embodiments as shown in Scheme 3, a compound of Formula 1 and a compound of Formula 7 are used for a coupling reaction in the presence of a Reagent B selected from trimethylamine, pyridine, and 3-picoline (or 3-methylpyridine) to form a compound of Formula 11. Next the compound of Formula 11 is neutralized with an acid to form the compound of Formula 10.

Subsequent addition of water and seed crystals can induce crystallization of desired polymorph form as previously disclosed.

Suitable acid can be an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some embodiments, the acid comprises hydrochloric acid (HCl). Other suitable acid can be an organic acid selected from formic acid, acetic acid, propionic acid, citric acid, malic acid, and sulfonic acids. In some embodiments, the acid comprises sulfonic acids. Examples of sulfonic acids including para-toluenesulfonic acid, methanesulfonic acid, and toluenesulfonic acid as a mixture of isomers. In some embodiments, the coupling step shown in Scheme 3 does not use a base. In some embodiments, the coupling step shown in Scheme 3 does not use any solvent comprising ethers, esters, and/or halogenated hydrocarbons.

Scheme 3

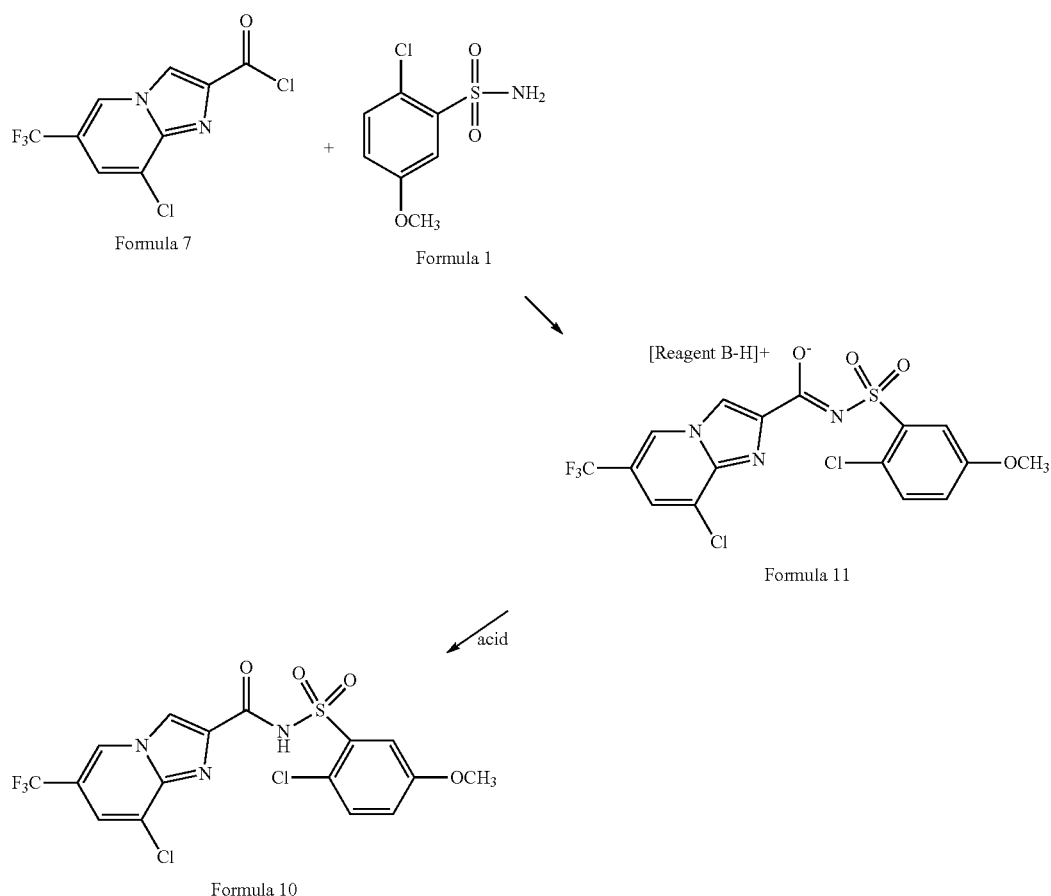

The coupling step shown in Scheme 3 can be accomplished in a solvent selected from water, $C_7$-$C_{10}$ aromatic hydrocarbons, $C_5$-$C_{10}$ aliphatic hydrocarbons, $C_5$-$C_{10}$ cycloaliphatic hydrocarbons, acetonitrile, or combinations thereof. In some embodiments, water, toluene, acetonitrile, or combinations thereof can be used. Other suitable solvent include xylenes, ethylbenzene, and cumene.

The coupling step shown in Scheme 3 can be run under a broad range of temperatures, i.e., temperatures in the range from 20° C. to 150° C.; or from 40° C. to 100 CC. Temperatures in the range from 50° C. to 100° C. are particularly useful. Temperatures in the range from 50° C. to 80° C.; or from 60° C. to 75° C. are especially useful.

The molar ratio of the compound of Formula 1 to the compound of Formula 7 can be in the range of 2:1 to 1:2; 1.5:1.0 to 1.0:1.5; 1.2:1.0 to 1.0:1.2; 1.1:1.0 to 1.0:1.1; and/or 1:1.

Again, the processes shown in Schemes 2 and/or 3 reduce the cost of production and avoid the use of a pyrophoric reagent as compared to previously disclosed processes. The processes shown in Scheme 2 and/or 3 also have other advantages including safer process by avoiding pyrophoric reagents, better volume efficiency, better reaction kinectics, reduced foaming problem, and/or a more efficient control of the Formula 10 polymorph that crystallizes as compared to previously disclosed processes (for example selecting different polymorph).

Preparation Example 1

Synthesis of Compound of Formula 3

To a 1 L round bottom flask equipped with an overhead mechanical stirrer, a 10 cm glass spring packing, a modified Dean-Stark trap, a thermometer, a condenser and a nitrogen inlet and outlet is charged p-anisidine (67 g; 0.539 mol) and o-dichlorobenzene (ODCB, 359.4 mL, 5.26 vol). 70% Sulfuric acid (98 wt %, 50.1 g, 27.2 ml, 0.501 mol) is added into 20 g of water and then added dropwise to the reactor while maintaining the internal temperature at <60° C. The reaction mixture was agitated for 30 min. The resulting gray white slurry was heated to 170° C. and reflux-distilled to remove water at atmospheric pressure. The reaction mass was agitated at 170-176° C. until the content of p-anisidine was <7%. The reaction mass is filtered and washed with o-dichlorobenzene. The compound of Formula 3 wet product (125.1 g, ~70 wt %, 0.431 mol) is obtained as a light gray solid with purity >97.5% by HPLC (High Performance Liquid Chromatography).

Preparation Example 2

Synthesis of Compound of Formula 4 and 5

To a 1 L round bottom flask equipped with an overhead stirrer, a thermocouple, and a nitrogen inlet/outlet is charged concentrated hydrochloric acid (30% wt %, 314.2 g, 261.8 mL, 2,585 mol) and water (76.7 mL, 0.88 vol). The compound of Formula 3 wet product (125.1 g, ~70 wt %, 0.431 mol) is added and the resulting slurry is cooled to <10° C. A solution of sodium nitrite (31.2 g, 98%, 0.444 mol) dissolved in water (87.6 mL) is added slowly and the reaction is stirred for 1 h. Sulfamic acid (2.1 g, 98%, 0.222 mol) is then dissolved in water (43.6 mL) and the solution is added to the reaction mass to form compound of Formula 4.

Water (87.6 ml) is then added to a second 1 L round bottom flask followed by copper powder (~150 mesh, 3.4 g, 0.054 mol) and the slurry stirred at room temperature. The reaction mass is transferred slowly to the copper slurry and agitated for about two hours.

The reaction mixture is cooled to <25° C. and then 50% NaOH aqueous solution (98% NaOH, 35.1 g, 2.0 mol, dissolved in 33.7 g of water) is added dropwise until pH reaches 2.5-3.5. The resulting dark yellow slurry is agitated for another two hours then filtered. After suction-dried the resulting compound of Formula 5 product (108.0 g, 0.353 mol) is obtained with purity >98% by HPLC.

Preparation Example 3

Synthesis of Compound of Formula 6

To a 1 L round bottom flask equipped with an overhead mechanical stirrer, a Dean-Stark trap, a thermometer, and a condenser is charged the compound of Formula 5 from the last example followed by toluene (432.1 mL). The resulting slurry is heated to remove water content. The slurry is cooled to 60-65° C. and N, N-dimethylformamide (4.1 mL, 0.053 mol) is added to the reactor followed by thionyl chloride (64.2 mL, 0.883 mol). After 2 h the reaction mass is distilled to ~½ the volume and toluene (259.3 mL) is added to the slurry followed by further distillation. The resulting slurry is filtered through a Celite pad (8.6 g) and the pad is washed with toluene (86.4 mL) where the filtrate gives compound for Formula 6.

Preparation Example 4

Synthesis of Compound of Formula 1

To a 1 L round bottomed flask is charged aqueous ammonia (28 wt %, 158.5 mL, 2.346 mol) and acetonitrile (176.7 ml) under a nitrogen atmosphere. The compound of Formula 6 from the last example is added to the solution and agitated for about two and half hours, resulting in two separate layers. The layers are separated and the lower aqueous layer is mixed with toluene (1.0 vol) and acetonitrile (1.0 vol) for further agitation, again resulting two separate layers. The combined organic layers are treated with activated carbon (3.0 wt %) and then filtered through a Büchner funnel and concentrated to afford compound of Formula 1, which is dried in a vacuum oven to give a light brown solid with purity >99% by HPLC.

Preparation Example 5

Synthesis of Compound of Formula 7

To a 100-mL 3-neck flask equipped with a condenser, addition funnel, thermocouple, heating mantle, and magnetic stirrer is charged a compound of Formula 8 (10.01 g, 37.5 mmol), acetonitrile (27 mL), and 3-picoline (2.824 g, 30.0 mmol). The mixture is heated to ~65° C., and then a solution of thionyl chloride (5.40 g, 44.9 mmol) in acetonitrile (3 mL) is added dropwise over ~20 minutes while maintaining the temperature between 63-71° C. After the addition is complete, the reaction mixture is heated at 70° C. for about two hours and then allowed to cool to ambient temperature to give compound of Formula 7 as a solution in acetonitrile.

Preparation Example 6

Synthesis of Compound of Formula 10—

Coupling Reaction Using Compounds of Formula 1 and 7

To a separate 125 mL 4-neck jacketed round bottom flask equipped with a magnetic stirrer, condenser, thermocouple and circulating bath, is charged compound of Formula 1 (10.05 g, 44.9 mmol), 3-picoline (8.462 g, 90.0 mmol), and acetonitrile (10 mL). The mixture is heated to ~58° C., and then the compound of Formula 7 is added dropwise via a peristaltic pump over ~1.5 hours while maintaining the reaction temperature between 55-60° C. The reaction is heated at ~60° C. for ~1 hr and then concentrated hydrochloric acid (~37% by weight, 3.895 g, 39.4 mmol) and water (0.5 mL) are then added to give to give an aqueous acetonitrile solution of Compound 10. The solution is heated to ~70° C. and then a slurry of Formula 10 seed crystals (0.195 g) in water (28 g) is added over ~2 hr. After adding more water (10 g), the resulting slurry is refluxed for ~1.5 hrs, cooled to ambient temperature, and then filtered. The wet cake is washed with aqueous acetonitrile and dried to give a compound of Formula 10 as an off-white to light brown solid in about 90% yield and ~98% purity.

What is claimed is:
1. A method of preparing a compound of Formula C:

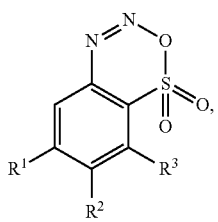

Formula C wherein each $R^1$, $R^2$, and $R^3$ is independently H, $SF_5$, $N(C_1-C_8$ alkyl$)(C_1-C_8$ alkyl), $C(=S)N(C_1-C_8$ alkyl$)(C_1-C_8$ alkyl), $SO_2N(C_1-C_8$ alkyl$)(C_1-C_8$ alkyl), $OSO_2(C_1-C_8$ alkyl), $OSO_2N(C_1-C_8$ alkyl$)(C_1-C_8$ alkyl), $N(C_1-C_8$ alkyl$)SO_2(C_1-C_8$ alkyl), or $C_1-C_8$ alkyl, $C_1-C_8$ haloalkyl, $C_2-C_8$ alkenyl, $C_2-C_8$ alkynyl, $C_3-C_{10}$ cycloalkyl, $C_3-C_{10}$ halocycloalkyl, $C_4-C_{10}$ alkylcycloalkyl, $C_4-C_{10}$ cycloalkylalkyl, $C_6-C_{14}$ cycloalkylcycloalkyl, $C_5-C_{10}$ alkylcycloalkylalkyl, $C_3-C_8$ cycloalkenyl, $C_1-C_8$ alkoxy, $C_1-C_8$ haloalkoxy, $C_3-C_8$ cycloalkoxy, $C_3-C_8$ halocycloalkoxy, $C_4-C_{10}$ cycloalkylalkoxy, $C_2-C_8$ alkenyloxy, $C_2-C_8$ alkynyloxy, $C_1-C_8$ alkylthio, $C_1-C_8$ alkylsulfinyl, $C_1-C_8$ alkylsulfonyl, $C_3-C_8$ cycloalkylthio, $C_3-C_8$ cycloalkylsulfinyl, $C_3-C_8$ cycloalkylsulfonyl, $C_4-C_{10}$ cycloalkylalkylthio, $C_4-C_{10}$ cycloalkylalkylsulfinyl, $C_4-C_{10}$ cycloalkylalkylsulfonyl, $C_2-C_8$ alkenylthio, $C_2-C_8$ alkenylsulfinyl, $C_2-C_8$ alkenylsulfonyl, $C_2$-$C_8$ alkynylthio, $C_2$-$C_8$ alkynylsulfinyl, $C_2$-$C_8$ alkynylsulfonyl, or phenyl; or two of $R^1$, $R^2$, and $R^3$ on adjacent ring atoms may be taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and such ring is optionally substituted with up to 3 substituents independently selected from the group consisting of $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl; and M is an inorganic cation or organic cation;
comprising:
(a) contacting a compound of Formula A

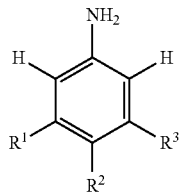

Formula A with a solvent selected from o-dichlorobenzene (ODCB), chloroalkanes, and chloroarenes, and a first acid selected from sulfonic acids, sulfuric acid ($H_2SO_4$), and oleum to form a compound of Formula B:

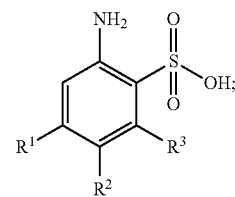

Formula B and
(b) contacting the compound of Formula B with (i) a nitrite salt $MNO_2$ or nitrite ester and (ii) a second acid selected from at least one inorganic acid, at least one organic acid, or mixtures thereof to form a compound of Formula C:

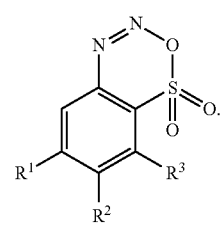

Formula C

2. The method of claim 1, wherein each $R^1$, $R^2$, and $R^3$ is independently H, $C_1$-$C_6$ alkyl, $C_1$-$C_6$ haloalkyl, $C_1$-$C_6$ alkoxy, $C_1$-$C_6$ haloalkoxy, or phenyl.

3. The method of claim 1, wherein $R^2$ is $CH_3$, $CH_2CH_3$, $CF_3$, $OCH_3$, $OCF_3$, or $OCH_2CH_3$.

4. The method of claim 1, wherein the second acid comprises an inorganic acid selected from hydrochloric acid (HCl), hydrobromic acid (HBr), phosphoric acid ($H_3PO_4$), sulfuric acid ($H_2SO_4$), and boric acid ($H_3BO_3$).

5. The method of claim 1, wherein the second acid comprises an organic acid selected from formic acid, acetic acid, propionic acid, citric acid, malic acid, and sulfonic acids.

* * * * *